United States Patent [19]

Tindberg

[11] Patent Number: 4,920,985
[45] Date of Patent: May 1, 1990

[54] DEVICE FOR CLOSING A CURVED DUCT

[75] Inventor: N Bertil E. Tindberg, Bjärred, Sweden

[73] Assignee: Peltor AB, Varnamo, Sweden

[21] Appl. No.: 223,242

[22] PCT Filed: Jan. 23, 1986

[86] PCT No.: PCT/SE86/00024
§ 371 Date: Sep. 19, 1988
§ 102(e) Date: Sep. 19, 1988

[87] PCT Pub. No.: WO87/04338
PCT Pub. Date: Jul. 30, 1987

[51] Int. Cl.$^5$ .............................................. A61F 11/00
[52] U.S. Cl. ...................................... 128/864; 128/865
[58] Field of Search .................................. 128/864–868

[56] References Cited

U.S. PATENT DOCUMENTS

| 2,262,568 | 11/1941 | Wade | 128/864 |
| 2,538,339 | 1/1951 | Thomas | 128/864 |
| 4,160,449 | 7/1979 | Wade | 128/864 |

Primary Examiner—Richard J. Johnson
Assistant Examiner—Charles H. Sam
Attorney, Agent, or Firm—Brooks & Kushman

[57] ABSTRACT

A device for closing a curved duct, especially an ear protector for insertion in the auditory canal (4) of the ear, consists of an elastic rod-shaped body (1), e.g. of foamed plastic, which is pointed at one end and the cross-sectional area of which is larger than that of the auditory canal. The pointed end of the rod-shaped body is considerably offset with respect to the longitudinal direction of the body so as to form a lip (5) which is unsymmetrical in relation to the longitudinal direction of the body and capable of conforming to the curved portion of the auditory canal when the rod-shaped body is inserted therein.

1 Claim, 1 Drawing Sheet

DEVICE FOR CLOSING A CURVED DUCT

The present invention relates to a device for closing a curved duct, especially an ear protector for insertion in the auditory canal of the ear. The device consists of an elastic rod-shaped body the cross-sectional area of which is larger than that of the auditory canal.

Today, there are available on the market a number of different ear protectors, so-called ear plugs, for insertion in the ear canal. However, all such prior art ear plugs suffer from more or less serious shortcomings. Thus, generally, the ear plugs have not been conformed to the shape of the auditory canal. The external auditory canal is curved and bends when approaching the eye. Prior art ear plugs are not capable of conforming to the auditory canal and cannot be inserted therein farther than the curved portion thereof. One prior art ear plug consists of a rod-shaped body of foamed plastic which is blunt at both ends and, therefore, difficult to insert in the auditory canal. Further, because of its blunt shape the plug will get stuck in the bend of the auditory canal. Another previously known ear plug has the form of a projectile with a pointed tip. Like the above-mentioned blunt ear plug, this ear plug is disadvantageous in that the tip of the plug gets stuck in the bend of the auditory canal instead of proceeding round the bend.

The object of the invention is to overcome the drawbacks inherent in the above-described plug designs by providing an ear plug which is adapted more readily to conform to the bend of the auditory canal and, thus, facilitates the insertion of the ear plug in the ear.

According to the invention, this object is achieved by a device of the above-described type having the features recited in the characterizing clause of the claim.

The invention will now be described in more detail hereinbelow in one embodiment with reference to the accompanying drawing.

Figure 1:
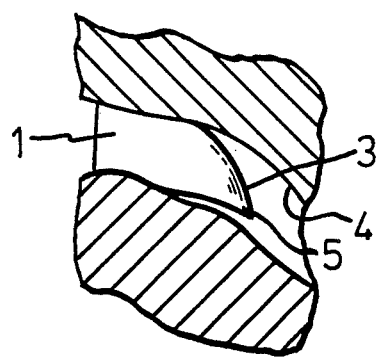
FIG. 1 is a section through a human ear and illustrates an ear plug according to the invention when inserted in the auditory canal.

FIG. 1 shows an auditory canal 4 in which the ear plug 1 according to the invention is inserted. The ear plug is in the form of a cylindrical rod-shaped body having an oblique end surface 3 allowing the ear plug to conform more easily to the curved portion of the auditory canal.

Figure 2:
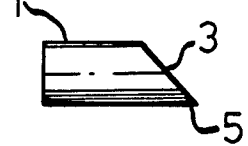
FIG. 2 shows the ear plug in a non-compressed state.

FIG. 2 shows the rod-shaped body 1 in a non-compressed state. The body consists of flexible foamed plastic, e.g. expanded polyurethane, PVC, expanded polyethylene and latex foam. The starting material is a long strand of such plastic material which is cut so that every other cut is made at right angles to the longitudinal direction of the strand and every other cut at an angle substantially less than 90° in relation to the said longitudinal direction. Alternatively, both cuts can be made at an angle substantially less than 90° in relation to the longitudinal direction. Another way of producing the rod-shaped bodies is stamping them from a sheet stock of a suitable plastic material and thereafter cutting one end of the stamped body to form the oblique end surface 3.

Figure 3:
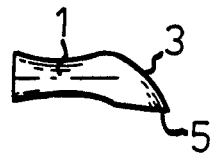
FIG. 3 shows the ear plug in a compressed state outside the ear.

The oblique cut of one end of the rod-shaped body produces a lip 5 thereon which is more flexible than the rest of the body. Experimentally, it has been found that this lip, upon radial compression of the body, will bend downwards, as seen in FIG. 3, which contributes to facilitating the insertion of the ear plug in the ear.

I claim:

1. An ear protector for insertion in the auditory canal (4) of a human ear, the device consisting of a compressible resilient rod-shaped body (1) having a pointed end (5) and a cross-sectional area which is slightly larger than the average cross-sectional area of the auditory canal in a non-compressed condition thereof, the improvement comprising: the pointed end (5) of the rod-shaped body is located in the circumferential surface of the body to form a lip which is unsymmetrical in relation to the longitudinal direction of the body (1) and the rod-shaped body bending to conform to the curved portion of the auditory canal when the body (1) is in a compressed condition to thereby facilitate insertion of the ear protector in the ear.

* * * * *